US005918594A

United States Patent [19]

Asking et al.

[11] Patent Number: 5,918,594

[45] Date of Patent: Jul. 6, 1999

[54] INHALER WITH DEAGGLOMERATING DEVICE

[75] Inventors: Lars Asking; Kjell Bäckström, both of Lund; Henri Hansson, Dösjebro; Magnus Jahnsson, Lund, all of Sweden

[73] Assignee: Astra Aktiebolag, Sodertalje, Sweden

[21] Appl. No.: 08/817,800

[22] PCT Filed: Jul. 23, 1996

[86] PCT No.: PCT/SE96/00969

§ 371 Date: Apr. 10, 1997

§ 102(e) Date: Apr. 10, 1997

[87] PCT Pub. No.: WO97/05917

PCT Pub. Date: Feb. 20, 1997

[30] Foreign Application Priority Data

Aug. 10, 1995 [SE] Sweden .................................. 9502799

[51] Int. Cl.$^{6}$ .................................................. A61M 15/00

[52] U.S. Cl. ................................ 128/203.15; 128/203.12; 128/203.23

[58] Field of Search ......................... 128/200.18, 203.15, 128/203.12, 203.23; 604/58; 222/636

[56] References Cited

U.S. PATENT DOCUMENTS

| | | | |
|---|---|---|---|
| 2,214,032 | 9/1940 | Stewart | 128/203.15 |
| 2,829,642 | 4/1958 | De Melfy | 128/203.15 |
| 2,992,645 | 7/1961 | Fowler | 128/203.15 |
| 3,795,244 | 3/1974 | Lax et al. | 128/203.15 |
| 4,046,146 | 9/1977 | Rosskamp et al. | 128/203.15 |
| 4,240,418 | 12/1980 | Rosskamp et al. | 128/203.15 |
| 4,739,754 | 4/1988 | Shaner | 128/203.15 |
| 4,907,583 | 3/1990 | Wetterlin et al. | 128/203.15 |
| 5,483,954 | 1/1996 | Mecikalski | 128/203.15 |
| 5,503,144 | 4/1996 | Bacon | 128/203.15 |
| 5,507,281 | 4/1996 | Kuhnel et al. | 128/203.15 |

FOREIGN PATENT DOCUMENTS

| | | |
|---|---|---|
| 0558879 A1 | 9/1993 | European Pat. Off. . |
| WO 92/04069 | 3/1992 | WIPO . |
| WO 93/17728 | 9/1993 | WIPO . |

OTHER PUBLICATIONS

"The Fluid Mechanics of Cromolyn Sodium Inhalers Used for Asthma Prevention", Niemi, Jr., Proceedings of 7$^{th}$ New England Bioeng. Conf., Troy, NY, USA. Mar. 20–23, 1979, pp. 33–36.

International–Type Search Report (3 pages) for SE 95/00797, Mar. 12, 1996.

*Primary Examiner*—Kimberly L. Asher
*Attorney, Agent, or Firm*—Fish & Richardson P.C.

[57] ABSTRACT

An inhalation device comprising means for breaking down aggregates of finely divided powdered medicament to provide medicament having a large number of particles within the respiratory range (less than 10 $\mu$m). The deaggregation means comprise at least two pairs of opposing surfaces in a gas/air flow path. The first pair define an inlet to a constricted region in the air flow path, and the second pair are located at or near the outlet of the constriction. The two pairs of surfaces are oriented at different angles with respect to the axis of the air flow path. In use, medicament particles carried by the gas/air flow impact the first pair of surfaces, then enter the constricted region where the speed of the gas/air flow is increased, and then impact the second pair of surfaces. The impacts break down agglomerations of the finely divided medicament, thereby delivering to the user a greater number of particles in the respiratory range.

14 Claims, 1 Drawing Sheet

INHALER WITH DEAGGLOMERATING DEVICE

TECHNICAL FIELD OF THE INVENTION

The present invention relates to an inhalation device comprising means for breaking down aggregates of finely divided powdered medicament having a particle size less than 10 μm to provide a large number of particles within the respiratory range, i.e. having particle sizes less than 10 μm.

BACKGROUND OF THE INVENTION

In inhalation therapy it is of utmost importance that the diameter of particles of the medicament to be inhaled is less than 10 μm to ensure the adequate penetration of the particles into the bronchial region of the lungs.

When the medicament is composed of particles having diameters less than 10 μm, the interparticular forces are generally greater than the force of gravity and consequently the material is cohesive. Non-defined agglomerates or aggregates form at random when this finely divided powdered medicament is handled, for instance during storage, conveying, sieving, sifting, mixing or grinding.

When using dry powder inhalers and especially breath-actuated dry powder inhalers it is therefore important that the inhalation device is provided with means which break down just before or during inhalation the said agglomerates or aggregates formed from the finely divided powder into the primary particles having a particles size within the respiratory range, of less than 10 μm, preferably less than 5 μm.

If the particle aggregates are bigger than 10 μm they will not penetrate to the bronchial region of the lungs but will end up in the oro-laryngeal tract or, if swallowed, in the gastrointestinal tract where they could lead to unwanted side-effects. Particle aggregates could also more easily be retained in the device which also leads to a loss of particles which will have a negative effect on the exactness of the doses.

Means for breaking down agglomerates/aggregates of powder created in finely divided powdered medicaments having a primary of less than 10 μm are known in the prior art. One example of such means is described in EP-B-069 715. In this document a rotating, propeller-like device is provided in the air conduit as deagglomeration means. Another example is described in EP-B-237 507, where a stationary deflector device is provided in the mouth-piece and/or the air conduit of a breath-actuated dry powder inhaler having a container for multiple doses. These stationary deflector devices will, during inhalation, provide a deaggregating effect as they are constructed to create a turbulent movement in the air flow carrying the substance. Due to this turbulent movement the particles will impact on the walls of the air conduit and the deflector devices and collide with each other and in this manner break down into primary within the respiratory range.

In WO 92/04069 a disposable breath-actuated dry powder inhaler for single use is disclosed. This inhaler is provided with means for breaking down agglomerates /aggregates in the air conduit. The deagglomerating means in this inhaler are also constructed to create a turbulent movement in the air flow during inhalation. This is achieved as all of the deagglomerating means are constructed as planar surfaces oriented about 30° relative to the longitudinal direction of the tubular housing of the inhaler.

Tests have shown that the above mentioned deaggregation means do not give an optimum deaggregation effect. In some cases retention in the inhaler could reach an unacceptable level. This could lead to different dosages with different inhalations.

SUMMARY OF THE INVENTION

It is therefore an object of the present invention to provide deaggregation means which optimize the deaggregation and which minimize the retention and the flow resistance at a typical gas or air flow rate which depends on the inhalation force of a patient.

According to the present invention there is provided an inhalation device comprising means for breaking down aggregates of primary particles of powder. The deaggregation means comprise at least two pairs of surfaces in a gas/flow path. The first pair define an inlet to a constricted region in the air flow path, and the second pair are located at or near the outlet of the constriction. The two pairs of surfaces are oriented at different angles with respect to the axis of the air flow path. In use, medicament particles carried by the gas/air flow impact the first pair of surfaces, then enter the constricted region where the speed of the gas/air flow is increased, and then impact the second pair of surfaces. The impacts break down agglomerations of the finely divided medicament, thereby delivering to the user a greater number of particles in the respiratory range.

Further preferred embodiments and advantages are clear from the claims.

BRIEF DESCRIPTION OF THE DRAWINGS

The device according to the present invention will now be described by way of example with reference to the appended drawings, wherein.

DETAILED DESCRIPTION OF THE DRAWINGS

It is generally known in powder technology that the breakdown of aggregates formed from powdered substances can be achieved by giving aggregates an acceleration prior to impact with a surface, for example walls placed in the direction of the movement of the aggregates. When this technology is applied to inhalation materials so-called deaggregation means are placed in the gas/air flow path of the inhalation device. Such deaggregation means can be provided as walls, as described in the above mentioned documents.

Tests have shown that the breakdown of aggregates into primary particles is related to the positions and angles of said surfaces as well as to the dimensions of the cross sections of the gas/air flow path of the inhaler at different positions. A preferred embodiment of the deaggregation means in accordance with the present invention will be described with reference to FIGS. 1, 2 and 3.

In the preferred embodiment deaggregation means of the present invention are designed to be placed in the gas/air flow path of a unit (single use) dose dry powder inhaler but the construction of the deaggregation means could easily be adapted to be placed in the gas/air flow path of any dry powder inhaler having a dose 8 which comprises aggregates of a powdered substance placed in an gas/air flow path 10, an air inlet 5 and an air outlet 6. Said air inlet 5 and air outlet 6 are positioned at a distance from each other, whereby the gas/air flow during inhalation will pass in said gas/air flow path between the air inlet and the air outlet thereby lifting the dose so that it can be carried along by the gas in the gas/air flow. The following description of the device is related to the preferred embodiment, but this embodiment is only offered as an example.

In the preferred embodiment several sets of oblique planar surfaces are provided along the gas/air flow path 10 in the inhaler. The dose 8 is placed in a magazine (not shown) which could be a unit dose magazine or a magazine which could be refilled for subsequent inhalations.

Said oblique surfaces provide constrictions in the gas/air flow path which will result in an acceleration of the inhalation gas/air flow and guidance during its passage through the gas/air flow path. The aggregates and/or particles will thereby be forced to impact on the walls and surfaces of the gas/air flow path.

In the preferred embodiments the deaggregafion means have substantially two different forms and constructions.

Figure 1:
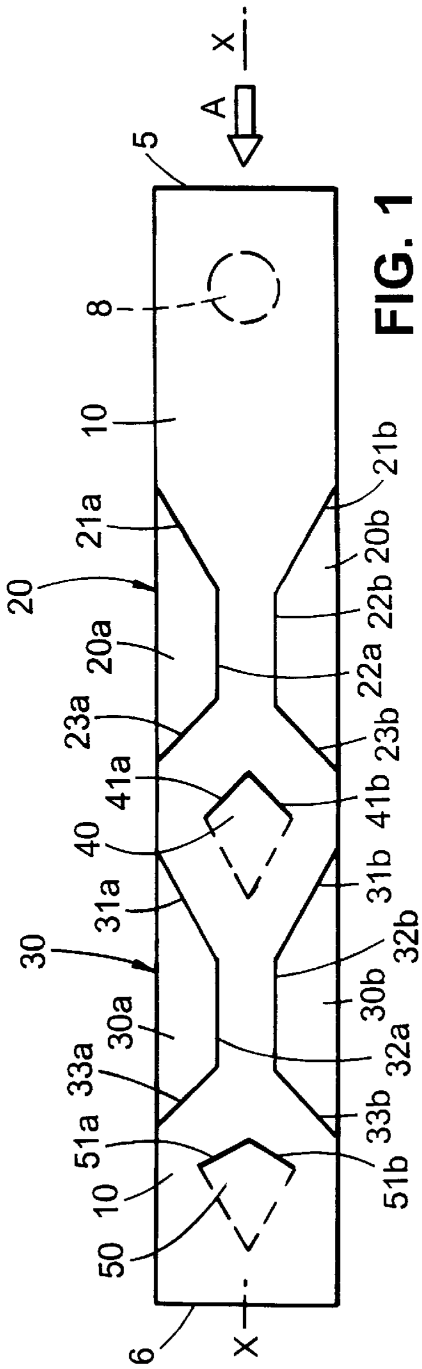
FIG. 1 shows a preferred embodiment of the deaggregation means according to the present invention.
Figure 2:
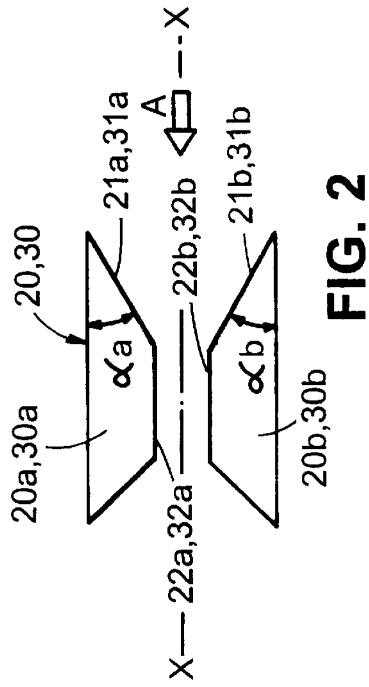
FIG. 2 shows first deaggregation means according to the invention as shown in FIG. 1.

As shown in FIGS. 1 and 2, the first deaggregation means 20 and 30 are formed as pairs of walls 21*a*, 21*b* and 31*a*, 31*b* respectively extending with an angle $\alpha_a$ and $\alpha_b$, respectively, to the main direction (Arrow A in the figures) of the gas/air flow and the longitudinal center axis of symmetry of the gas/air flow path 10 and the device seen from the air inlet 5 to the air outlet 6. Said longitudinal center axis is marked with X—X in FIGS. 1–3. Preferably said pairs of walls extend from the edges of the housing on both sides of the gas/air flow path symmetrically and are spaced apart so as to provide a passage for the gas/air flow and a restriction in the gas/air flow path. The first pair of walls 21*a*, 21*b* are placed adjacent to the release area of the dose 8. Said pairs of walls 21*a*, 21*b* and 31*a*, 31*b* are connected to a part 22*a*, 22*b* and 32*a*, 32*b* respectively being longitudinal in the main direction A of the gas/air flow. Said longitudinal parts extend parallel to the main direction A of the gas/air flow and are spaced apart so as to provide a passage for the gas/air flow. The other end of said longitudinal parts 22*a*, 22*b* and 32*a*, 32*b* are connected to a wall 23*a*, 23*b* and 33*a*, 33*b* respectively which together with the first wall and the longitudinal part of each deaggregation means form the quadrangle-shaped deaggregation means 20, 30. In FIGS. 1 and 2 a preferred embodiment of these first deaggregation means are shown. The angle and form of the walls 23*a*, 23*b* and 33*a*, 33*b* are only of importance for the construction and geometry of the deaggregation means and the gas/air flow path and is not important for the function of the device. The important feature for the function is the aim to minimize the retention of substance in the gas/air flow path. Therefore any angle and/or form of said walls having this function can be used.

The second deaggregation means 40, 50 are formed as pairs of walls 41*a*, 41*b* and 51*a*, 51*b* respectively. The two walls in each pair of walls are connected to each other and form a tip or point 42, 52 respectively. Said tip or point 42, 52 is provided in the center of the gas/air flow path 10 and coincides with the longitudinal axis of symmetry X—X of the gas/air flow path and also with the main direction A of the gas/air flow seen from the air inlet 5 to the air outlet 6.

Figure 3:
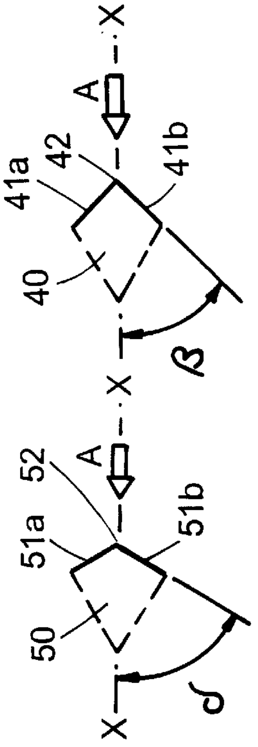
FIG. 3 shows the two bodies of the second deaggregation means according to the invention as shown in FIG. 1.

The impact surfaces 41*a*, 41*b* and 51*a*, 51*b* of said deaggregation means are provided at angles β and δ, respectively, to the main direction A of the gas/air flow and the longitudinal axis of symmetry X—X of the gas/air flow path and the device seen from the air inlet 5 to the air outlet 6. The preferred embodiment of the second deaggregation means 40 and 50 are shown in FIG. 3.

The first and second deaggregation means 20, 30 and 40, 50 are positioned in the gas/air flow path in a manner which give rise to acceleration areas for the gas/air flow and the aggregates/particles as well as guidance whereby the aggregates and particles are forced to impact on the walls of said deaggregation means.

The preferred forms of the deaggregation means has been determined by tests and the most optimal forms for the above mentioned purpose have shown to be the ones represented in FIG. 1. The forms of the deaggregation means are also important for minimizing retention of substance in the gas/air flow path as well as the gas/air flow resistance of an inhaler in which the deaggregation means are provided. For example if the deaggregation means are formed as triangles with the tip of the triangles facing the direction of the air flow during inhalation the backside of the means will have a generally flat surface positioned perpendicular to the inhalation air flow. This will give rise to substantial retention.

The tests have shown that the values of the angles $\alpha_a$, $\alpha_b$ and especially the values of the angles β and δ are of utmost importance for good functioning of the deaggregation means and thereby the functioning of the inhaler. Several tests have been done with different substances and the optimum values of the angles have been determined as a function of the different parameters which influences the performance of the gas/air flow during inhalation. It has thereby been important to minimize retention of substance and the flow resistance as well as maximize the deaggregation at a typical gas/air flow rate which depends on the inhalation force of a patient.

Earlier tests have shown that the $\alpha_a$ and $\alpha_b$ should be substantially about 30° to the main direction of the gas/air flow seen from the air inlet to the air outlet and to a longitudinal axis being parallel to the longitudinal axis of symmetry of the device. The choice of 30° for these angles is dependent on minimizing the flow resistance and retention of substance as well as optimizing the acceleration of the air/gas flow upon entry into the first constriction in the gas/air flow path.

The optimum value of the angle β is substantially about 45° to the main direction of the gas/air flow as seen from the air inlet to the air outlet and to the longitudinal axis of the device.

The value of the angle β is substantially about 60° to the main direction of the gas/air flow as seen from the air inlet to the air outlet and to the longitudinal axis of the device.

The choice of these values is based on test results, a summary of which is shown below.

Summary of the Results from Tests Carried Out in Order to Determine the Optimum Values of the Angles β and δ:

Several tests have been carried out in order to determine the optimum values of the angles of the second and third deagglomeration means, i.e. the angles β and δ. Below a summary of the results from these test are shown in tables.

In all tests the first angles $\alpha_a$ and $\alpha_b$ have been kept constant at 30° in order to provide a smooth entry for the gas/air flow into the gas/air flow path. Tests were carried out using substances having different properties. The substances used in each test are indicated in the table.

In order to be able to compare the results from the different tests an index was introduced. Said index is based on the following calculation:

$$I=(F^2\div(Re*C))*10000$$

where I is the Index, F is the fraction of fine particles, Re is the retention in percentage of total dose, and C is the inhalation resistance (C-value). The result is multiplied by 10,000 to provide an easy to read value for the index.

Study 1.

TABLE 1

In this study, one substance - tertbutalinesulphate - was used. The aim of the tests was to determine the relationship between the values of the angles β and δ.

| Test No. | Value of angles $\alpha_a$, $\alpha_b$ | Value of angle β | Value of angle δ | Fraction of fine particles (F) | Retention (% of total dose) | Inhalation resistance (C-value) | Index (I) |
|---|---|---|---|---|---|---|---|
| 1 | 30° | 75° | 60° | 44 | 18 | 15395 | 70 |
| 2 | 30° | 45° | 60° | 44 | 15 | 14424 | 89 |
| 3 | 30° | 75° | 21° | 36 | 18 | 14765 | 70 |
| 4 | 30° | 45° | 21° | 35 | 14 | 12488 | 49 |
| 5 | 30° | 60° | 30° | 43 | 21 | 12825 | 69 |

As can be seen test no. 2 with β being 45° and δ being 60° showed the highest index. Test no. 4 with β being 45° and δ being 21° showed the lowest index. This indicates that β<δ is more favourable then β>δ.

Study 2.

In this test, three different substances, terbutalinesulphate, budenoside and formoterol mixed with lactose, were used. The aim of the tests was to determine whether an optimum vallue of the angles could be found in the range 21°–75°.

TABLE 2

Substance: terbutalinesulphate

| Test No. | Value of angles $\alpha_a$, $\alpha_b$ | Value of angle β | Value of angle δ | Fraction of fine particles (F) | Retention (% of total dose) | Inhalation resistance (C-value) | Index (I) |
|---|---|---|---|---|---|---|---|
| 1 | 30° | 21° | 21° | 24 | 8 | 10630 | 71 |
| 2 | 30° | 75° | 21° | 24 | 11 | 11110 | 50 |
| 3 | 30° | 45° | 45° | 32 | 11 | 12420 | 76 |
| 4 | 30° | 21° | 75° | 37 | 12 | 13120 | 86 |
| 5 | 30° | 75° | 75° | 40 | 11 | 14000 | 107 |

TABLE 3

Substance: budenoside

| Test No. | Value of angles $\alpha_a$, $\alpha_b$ | Value of angle β | Value of angle δ | Fraction of fine particles (F) | Retention (% of total dose) | Inhalation resistance (C-value) | Index (I) |
|---|---|---|---|---|---|---|---|
| 1 | 30° | 21° | 21° | 17 | 12 | 10630 | 22 |
| 2 | 30° | 75° | 21° | 22 | 22 | 11110 | 20 |
| 3 | 30° | 45° | 45° | 27 | 17 | 12420 | 36 |
| 4 | 30° | 21° | 75° | 37 | 28 | 13120 | 39 |
| 5 | 30° | 75° | 75° | 43 | 31 | 14000 | 42 |

TABLE 4

Substance: formoterol mixed with lactose

| Test No. | Value of angles $\alpha_a$, $\alpha_b$ | Value of angle β | Value of angle δ | Fraction of fine particles (F) | Retention (% of total dose) | Inhalation resistance (C-value) | Index (I) |
|---|---|---|---|---|---|---|---|
| 1 | 30° | 21° | 21° | 31 | 16 | 10630 | 58 |
| 2 | 30° | 75° | 21° | 42 | 28 | 11110 | 58 |
| 3 | 30° | 45° | 45° | 49 | 21 | 12420 | 90 |

TABLE 4-continued

Substance: formoterol mixed with lactose

| Test No. | Value of angles $\alpha_a$, $\alpha_b$ | Value of angle β | Value of angle δ | Fraction of fine particles (F) | Retention (% of total dose) | Inhalation resistance (C-value) | Index (I) |
|---|---|---|---|---|---|---|---|
| 4 | 30° | 21° | 75° | 51 | 27 | 13120 | 74 |
| 5 | 30° | 75° | 75° | 63 | 30 | 14000 | 86 |

The Results of these tests also showed that β<δ gave a better result than β>δ. The value of β does not influence the result to a significant extent but the result for β=45° and δ=45° was better than expected. In fact this was the best combination for the substance formoterol mixed with lactose.

The results obtained in the first two studies show that 45° seem to be the optimum valve for angle β.

Study 3.

This study was carried out in order to determine the upper limit of the value of the angle δ. The substances used were conditioned and unconditioned terbutalinesulphate

TABLE 5

Substance: conditioned terbutalinesulphate

| Test No. | Value of angles $\alpha_a$, $\alpha_b$ | Value of angle β | Value of angle δ | Fraction of fine particles (F) | Retention (% of total dose) | Inhalation resistance (C-value) | Index (I) |
|---|---|---|---|---|---|---|---|
| 1 | 30° | 45° | 60° | 49 | 14 | 13342 | 129 |
| 2 | 30° | 45° | 70° | 49 | 20 | 14825 | 81 |
| 3 | 30° | 45° | 75° | 52 | 17 | 15502 | 103 |
| 4 | 30° | 45° | 80° | 50 | 22 | 15183 | 75 |
| 5 | 30° | 45° | 85° | 52 | 23 | 15482 | 76 |
| 6 | 30° | 45° | 90° | 26 | 16 | 15872 | 83 |

TABLE 6

Substance: unconditioned Terbutalinesulphate

| Test No. | Value of angles $\alpha_a$, $\alpha_b$ | Value of angle β | Value of angle δ | Fraction of fine particles (F) | Retention (% of total dose) | Inhalation resistance (C-value) | Index (I) |
|---|---|---|---|---|---|---|---|
| 1 | 30° | 45° | 60° | 53 | 11 | 13342 | 191 |
| 2 | 30° | 45° | 75° | 49 | 12 | 15502 | 129 |
| 3 | 30° | 45° | 90° | 55 | 13 | 15872 | 147 |

The Results of these tests also showed that the best results are achieved with the values of the angles β and δ being 45° and 60°, respectively.

The results of the above described tests gave the basis for choosing the following values for the angles in the inhalation device according to the present invention: $\alpha_a$ and $\alpha_b$ being 30°, β being 45° and δ being 60°.

The device according to the invention is simple to produce. It is preferably produced in two pieces, a first substantially flat part and a second part in which the air flow path with the constrictions and the deaggregation parts are formed during a molding or cold forming procedure. The two parts are then connected to each other in a manner that provides an air tight seal between the two parts. For this purpose heat- or cold-sealing, laser-welding or ultra sonic welding could be used as well as any other suitable sealing method. The two parts of the device are preferably made of plastic material but any other material in which the required air flow path can be easily formed can be used. The device could also be formed by two identical parts which are sealingly connected to each other. This, however, would be a more complicated method.

It is also possible to produce the device in one part whereby injection molding or blow molding could be used.

Modifications

The device according to the invention as described above can of course be modified within the scope of the appended claims.

Thus in the preferred embodiment the first and second deagglomeration means are formed as quadrangles having the described form. It is however clear that the form of the deagglomeration means can be varied. For example, the "backside" of the deagglomeration means can have any form which preferably does not give rise to a significant reduction in the speed of the gas/air flow or substantial retention of substance as mentioned above. The second deagglomeration means could for example be formed as triangles or be V-formed whereby the top of the triangle or the tip of the V is placed in the center of the gas/air flow path of the device.

The values of angles $\alpha_a$, $\alpha_b$ and $\beta$, $\delta$ could be changed although the performed tests show that the optimum values of these angles are the ones stated above.

In addition, the deaggregation means can be modified to be used in any powder inhaler, in particular any dry powder inhaler. Alternative embodiments and modifications not discussed herein are within the appended claims.

We claim:

1. An inhalation device comprising:

a dose of finely divided powdered medicament having a particle size of less than 10 $\mu$m;

a housing defining an air flow path for delivery of said dose to a patient;

a deagglomerating device, disposed in the air flow path and constructed to break down aggregates present in the finely divided powdered medicament, comprising (a) a pair of opposing first surfaces oriented obliquely to a longitudinal direction of the air flow path and located on opposite sides of the air flow path which provide a constriction in the air flow path to increase the speed of air passing along the air flow path, and (b) a pair of associated second surfaces positioned in an outlet region of the constriction and in the center of the air flow path, and oriented obliquely to the longitudinal direction of the air flow path to provide an impact surface, where said pairs of first and second surfaces are oriented at different angles to the longitudinal direction of the air flow path.

2. The device of claim 1 comprising at least two sets of said pairs of first and second surfaces, said sets being arranged in series and spaced so that the speed of the air along the air flow path leaving the first constriction is reduced before the air reaches the second constriction.

3. The device of claim 2 wherein each surface of the first pair of second surfaces is at an angle $\beta$ relative to the longitudinal axis of the housing taken in the direction of airflow through the housing, and each surface of the second pair of second surfaces is at an angle $\delta$ relative to the longitudinal axis of the housing taken in the direction of air flow through the housing, wherein the angle $\beta$ is about 45° and the angle $\delta$ is about 60°.

4. The device of claim 3 wherein said first surfaces are oriented at angles $\alpha_a$, $\alpha_b$ respectively, relative to the longitudinal axis of the housing taken in the direction of the air flow through the housing, and the angles $\alpha_a$, $\alpha_b$ are each about 30°.

5. The device of claim 1 further comprising a pair of third surfaces disposed in the outlet region of said constriction, diverging from said constriction to the housing walls defining the air flow path.

6. The device of claim 5 wherein said third surfaces are both oriented at an angle of about 30° relative to the longitudinal axis of the housing in the direction of air flow through the housing.

7. The device of claim 1 wherein said second surfaces are positioned symmetrically with respect to each other about the longitudinal center axis of the housing.

8. The device of claim 1 wherein a pair of opposing longitudinal parts which are substantially parallel to each other and positioned substantially parallel to the longitudinal axis of the housing on opposite sides of the air flow path between said first surfaces and said second surfaces, defining a constricted region of the air flow path which is approximately as narrow as the constriction defined by said first surfaces.

9. The device of claim 8 further comprising a pair of third surfaces disposed in the outlet region of said constricted region defined by the longitudinal parts, diverging from said longitudinal parts to the housing walls defining the air flow path.

10. The device of claim 1 wherein said device is a dry powder inhaler.

11. The device of claim 1 wherein said device comprises a plurality of doses of said powdered medicament.

12. The device of claim 1 wherein said powdered medicament comprises an active ingredient and a carrier for said active ingredient.

13. The device of claim 1 wherein said first surfaces are oriented at angles $\alpha_a$, $\alpha_b$ respectively, relative to the longitudinal axis of the housing taken in the direction of the air flow through the housing, and the angles $\alpha_a$, $\alpha_b$ are each about 30°.

14. A method of deagglomerating a finely divided powder during delivery of the powder to a patient through an inhaler comprising:

(a) providing an inhaler comprising (i) a dose of finely divided powdered medicament, (ii) a housing defining an air flow path for delivery of said dose to a patient, and (iii) a deagglomerating device, disposed in the air flow path and constructed to break down aggregates present in the finely divided powdered medicament, comprising a pair of opposing first surfaces oriented obliquely to a longitudinal direction of the air flow path and located on opposite sides of the air flow path which provide a constriction in the air flow path to increase the speed of air passing along the flow path, and a pair of associated second surfaces positioned in an outlet region of the constriction and in the center of the air flow path, and oriented obliquely to the longitudinal direction of the air flow path to provide an impact surface; and (b) causing a patient to inhale through the inhaler, drawing said dose through said deagglomerating device.

* * * * *